United States Patent [19]

Hansenne et al.

[11] Patent Number: 5,547,658
[45] Date of Patent: Aug. 20, 1996

[54] COSMETIC COMPOSITION CONTAINING MELANINLIKE PIGMENTS IN COMBINATION WITH CERTAIN TOCOPHEROLS, AND PROCESS FOR PROTECTING THE SKIN, HAIR, MUCOSAE AND COSMETIC COMPOSITIONS

[75] Inventors: Isabelle Hansenne, Paris; Serge Forestier, Claye-Souilly; Quang L. N'Guyen, Antony, all of France

[73] Assignee: L'Oreal, Paris, France

[21] Appl. No.: 26,059

[22] Filed: Mar. 3, 1993

[30] Foreign Application Priority Data

Mar. 3, 1992 [FR] France .................... 92 02532

[51] Int. Cl.⁶ ............... A61K 7/42; A61K 7/40; A61K 9/10
[52] U.S. Cl. ............... 424/59; 424/60; 514/937
[58] Field of Search ............................ 424/59

[56] References Cited

U.S. PATENT DOCUMENTS

| | | | |
|---|---|---|---|
| 4,144,325 | 3/1979 | Voyt | 424/59 |
| 4,508,706 | 4/1985 | Pawelek | 424/60 |
| 4,515,773 | 5/1985 | Herlihy | 424/59 |
| 4,806,344 | 2/1989 | Gaskin | 424/59 |
| 4,968,497 | 11/1990 | Wolfram et al. | 424/59 |
| 5,053,053 | 10/1991 | De Labbey et al. | 8/423 |

FOREIGN PATENT DOCUMENTS

| | | | |
|---|---|---|---|
| 0456545 | 11/1991 | European Pat. Off. | A61K 7/42 |
| 0467767 | 1/1992 | European Pat. Off. | A61K 7/13 |
| 2666226 | 3/1992 | France | A61K 7/42 |
| 2207153 | 1/1989 | United Kingdom | A61K 7/13 |

*Primary Examiner*—Shelley A. Dodson
*Attorney, Agent, or Firm*—Jacobson, Price, Holman & Stern, PLLC

[57] ABSTRACT

Cosmetic composition containing melaninlike pigments in combination with certain tocopherols, and process for protecting the skin, hair, mucosae and cosmetic compositions.

The present invention relates to a cosmetic composition comprising the combination of certain tocopherols bn with at least one melaninlike pigment derived from natural or synthetic sources, in a cosmetically acceptable carrier, and to a process for protecting the skin, mucosae, hair and cosmetic compositions against free radicals.

16 Claims, No Drawings

COSMETIC COMPOSITION CONTAINING MELANINLIKE PIGMENTS IN COMBINATION WITH CERTAIN TOCOPHEROLS, AND PROCESS FOR PROTECTING THE SKIN, HAIR, MUCOSAE AND COSMETIC COMPOSITIONS

The present invention relates to a cosmetic composition comprising melaninlike pigments in combination with certain tocopherols, aimed especially at protecting the human epidermis, the mucosae and the hair against free radicals, and to a process for protecting the human epidermis, the mucosae and the hair and cosmetic compositions against these radicals.

Solar radiation, heat, atmospheric pollution and especially smoke and tobacco are known to result in the formation of free radicals. These free radicals initiate degradation reactions of the lipids, proteins and nucleic acids which are present especially in the skin, the mucosae and hair. In addition, cosmetic compositions include constituents which are sensitive to free radicals, and especially lipids.

It has therefore appeared particularly important to protect the skin, the mucosae and hair from these free radicals.

Vitamin E is a known antioxidant for protecting the phospholipids of the cell membrane (J. B. Chazan and M. Szulc-Radicaux Libres et Vitamine E [Free Radicals and Vitamin E], Cah. Nutr. Diet. 1987, XXII, 1, pages 66–76) and its properties as agents against free radicals (AFR) are known.

Furthermore, certain melaninlike pigments have already been employed in cosmetic compositions for protecting the human epidermis against UV rays, making-up the skin, the eyelashes and the eyebrows or else coloring the hair, where their protective role against solar radiation has been established.

According to the invention it has been surprisingly discovered that the combination of melaninlike pigments with certain tocopherols, in a cosmetic composition, makes it possible to obtain very good results in terms of activity against free radicals. The activity of the combination against free radicals is, in fact, more active than each of the components, vitamin E, on the one hand, or the melaninlike pigments, on the other hand, when the latter are taken separately, at comparable concentrations.

The subject of the present invention is therefore a cosmetic composition comprising the combination of certain tocopherols with at least one melaninlike pigment, in a cosmetically acceptable carrier.

The tocopherols according to the invention are chosen from α-tocopherol, β-tocopherol, γ-tocopherol and δ-tocopherol and their isomers. α-Tocopherol, preferred according to the invention, is vitamin E. It exists in the forms of D-α-tocopherol, L-α-tocopherol and DL-α-tocopherol. DL-α-tocopherol is marketed in particular by Hoffmann La Roche. A mixture of α-tocopherol, β-tocopherol, γ-tocopherol and δ-tocopherol in a ratio of 25/25/25/25, dissolved in soya oil at a concentration of 50% is marketed under the name "Tocopherol Concentrat Naturel" by Rossow.

The activity against free radicals, which is improved in the combination according to the invention when compared with the activity of vitamin E, on the one hand, or that of the melaninlike pigments, on the other hand, has been demonstrated by the "Head Space" method (Q.L. N-Guyen et al., Symposium of AFECG-SFC, Bordeaux, May 1984, p. 358–359, Evaluation de l'oxydation aldé-hydique dans les produits cosmétiques [Evaluation of aldehyde oxidation in cosmetic products]; K. Warner et al., Journal of Food Science, 1974, V.39, p.761–765, Pentane formation and rancidity in vegetable oils). This method makes it possible to evaluate the percentage inhibition of the oxidation of vitamin F, itself highly oxidizable, by the product to be tested.

Melaninlike pigments have a mean diameter of between 10 nm and 50,000 nm, preferably between 30 nm and 20,000 nm.

The melaninlike pigment(s) are derived from natural or synthetic sources and can be obtained (A) by oxidation of at least one indolelike compound, (B) by oxidizing or enzymatic polymerization of melaninlike precursors, (C) by extraction of melanin from natural substances containing it, or (D) by culture of microorganisms which produce melanin.

The tocopherols of the invention are advantageously present in the cosmetic composition according to the invention by themselves or mixed, in a concentration of between 0.02 and 10% by weight relative to the total weight of the composition, and preferably between 0.02% and 6%.

The melaninlike pigments are advantageously present in the cosmetic composition according to the invention in a concentration of between 0,001 and 2%, preferably between 0,005 and 0.5% by weight relative to the total weight of the composition.

The tocopherol/melaninlike pigment weight ratio may be envisaged between 0.1 and 100, preferably 0.5 to 50.

According to the invention the pigments may be chosen from melaninlike pigments obtained by oxidation of an indolelike compound, by oxidizing or enzymatic polymerization of melaninlike precursors, by extraction of melanin from natural substances or by culture of microorganisms which produce melanin.

(A) In the first place, the melaninlike pigments can be obtained by oxidation of at least one indolelike compound chosen especially from those corresponding to the formula (I):

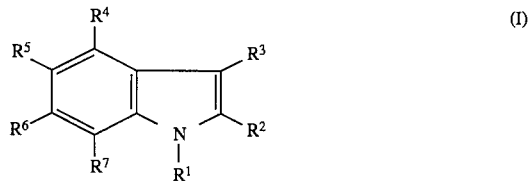

in which:
- $R^1$ and $R^3$ denote, independently of one another, a hydrogen atom or a $C_1$–$C_4$ alkyl group;
- $R^2$ denotes a hydrogen atom, a $C_1$–$C_4$ alkyl group, a carboxyl group or a $C_1$–$C_4$-alkoxycarbonyl group;
- $R^4$ and $R^7$ denote, independently of one another, a hydrogen atom, a hydroxyl group, a $C_1$–$C_4$ alkyl group, an amino group, a $C_1$–$C_4$ alkoxy group, a $C_2$–$C_4$ acyloxy group or a $C_2$–$C_4$ acylamino group;
- $R^5$ denotes a hydrogen atom, a hydroxyl group, a $C_1$–$C_4$ alkoxy group, a $C_1$–$C_4$ alkyl group, a halogen atom, an amino group, a $C_2$–$C_{14}$ acyloxy group, a $C_2$–$C_4$ acylamino group or a trimethylsilyloxy group;
- $R^6$ denotes a hydrogen atom, a hydroxyl group, a $C_1$–$C_4$ alkoxy group, an amino group, a $C_2$–$C_4$ acyloxy group, a $C_2$–$C_4$ acylamino group, a trimethylsilyloxy group or a $C_2$–$C_4$ hydroxyalkylamino group;
- it being also possible for $R^5$ and $R^6$ to form, together with the carbon atoms to which they are attached, a methylenedioxy ring optionally substituted by a $C_1$–$C_4$ alkyl or $C_1$–$C_4$ alkoxy group, or else a carbonyldioxy ring;
- at least one of the radicals $R^4$ to $R^7$ denotes a group OZ or $NHR^0$, not more than one of the radicals $R^4$ to $R^7$ denoting NHR⁰ and not more than two of the radicals $R^4$ to $R^7$ denoting OZ and, in the case where Z denotes a hydrogen atom, the two OH groups are in positions 5 and 6; and at least one of the radicals $R^4$ to $R^7$ denotes a hydrogen atom, and in the case where only one of these radicals denotes a hydrogen atom, only one radical among the radicals $R^4$ to $R^7$ then denotes NHR⁰ or OZ, the other radicals denoting a $C_1$–$C_4$ alkyl group;

the radical $R^0$ of the group NHR⁰ denoting a hydrogen atom, a $C_2$–$C_4$ acyl or $C_2$–$C_4$ hydroxyalkyl group, and the radical Z of the group OZ denoting a hydrogen atom, a $C_2$–$C_{14}$ acyl group, a $C_1$–$C_4$ alkyl group or a trimethylsilyl group, and their alkali metal, alkaline-earth metal, ammonium or amine salts.

The indolelike compounds of formula (I) above are preferably chosen from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methyl indole, 2-carboxy- 6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy- 6-hydroxyindole, 5-hydroxy-2-ethoxycarbonylindole, 6-hydroxy-2-carboxy-5methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5 -trimethylindole, 6-amino-2,3,6-trimethylindole, 5,6-diacetoxyindole, 5-methoxy-6acetoxyindole, 5,6-dimethoxyindole, 5,6-methylenedioxyindole, 5,6-trimethylsilyloxyindole, the phosphoric ester of 5,6-dihydroxyindole, 5,6-dibenzyloxyindole, and the addition salts of these compounds.

5,6-Dihydroxyindole is particularly preferred.

The oxidation of the indolelike compound of formula (I) may be performed in an aqueous or watersolvent(s) medium, in air, and in the presence or otherwise of an alkaline agent and/or of a metallic oxidation catalyst such as, for example, the cupric ion.

The reaction medium preferably consists of water and may, if appropriate, consist of a mixture of water and of at least one solvent chosen so that it rapidly dissolves the indolelike compound of formula (I). Among these solvents there may be mentioned, by way of examples, lower $C_1$–$C_4$ alcohols such as ethyl alcohol, propyl or isopropyl alcohol, tert-butyl alcohol, alkylene glycols such as ethylene glycol, propylene glycol, alkylene glycol alkyl ethers such as ethylene glycol monomethyl, monoethyl and monobutyl ethers, propylene glycol and dipropylene glycol monomethyl ethers and methyl lactate.

The oxidation may also be performed by using hydrogen peroxide in the presence of an alkaline agent such as, preferably, aqueous ammonia, or in the presence of an iodide ion, the iodide being preferably an alkali metal, alkaline-earth metal or ammonium iodide.

The oxidation may also be undertaken by employing periodic acid and its water-soluble salts and derivatives, permanganates and dichromates such as those of sodium or potassium, sodium hypochlorite, potassium ferricyanide, ammonium persulfate, silver oxide, lead oxide, ferric chloride, sodium nitrite, rare-earth salts including especially those of cerium, and organic oxidizing agents chosen from ortho- and para-benzoquinones, ortho- and para-benzoquinone mono- or diimines, 1,2- and 1,4-naphthoquinones, and 1,2- and 1,4-naphthoquinone mono- or diimines such as defined in Application EP-A-0,376,776. The preferred periodic acid salt is sodium periodate.

It is possible to activate the oxidizing agents using a pH modifier.

An enzymatic oxidation can also be envisaged.

The insoluble product is isolated by filtration, centrifuging, freeze-drying or spray-drying. It is then ground or micronized to reach the desired particle size.

(B) The melaninlike pigments according to the invention can also originate from the oxidizing or enzymatic polymerization of melaninlike precursors such as L-tyrosine, L-dopa, catechol and their derivatives.

(C) The melaninlike pigments according to the invention can also originate from the extraction of melanin from natural substances such as human hair, the ink of cephalopods (cuttlefish, octopuses), also known by the name of sepiomelanin, in which case the pigment is ground and purified before being employed.

(D) Finally, the melaninlike pigments according to the invention can be obtained by culture of microorganisms. These microorganisms produce melanin either naturally or by genetic modification or by mutagenesis. Methods of preparations of these melanins are described, for example, in Patent Application WO90/04029.

The melaninlike pigment(s) may be present at the surface or incorporated into an inorganic or organic, inert particulate filler, to constitute a synthetic composite melaninlike pigment formed in situ. In this case the melaninlike pigment(s) may result from the oxidation of at least one indolelike compound of formula (I), as defined above, mixed with the filler in a medium which is essentially a nonsolvent for the said filler, at a temperature which can range from room temperature to approximately 100° C., or else can result from the oxidizing polymerization of melaninlike precursors on the filler.

The general conditions for the oxidation of the indolelike compounds of formula (I) are the same as those mentioned above.

According to a first embodiment, the particulate filler is an inert inorganic filler advantageously consisting of particles with a particle size smaller than 20,000 nm. Such composite melaninlike pigments deposited on an inorganic filler are described, as is their preparation, in French Patent Application FR-A-2,618,069.

According to a second embodiment of the present invention, the particulate filler is an inert polymeric filler advantageously chosen from organic or inorganic, natural or synthetic polymers with a crystalline or amorphous, crosslinked network, which has a molecular weight of between 5000 and 5,000,000. Composite melaninlike pigments on a polymeric filler and their preparation are described in Luxembourgian Patent No. 87,429.

The organic or synthetic polymers are, in particular, chosen from the polymers derived from keratin, silk fibroin, chitin or cellulose, or from polyamides or the homo- or copolymers resulting from the polymerization of aliphatic or aromatic, mono- or polyethylenic monomers, with a crystalline or amorphous, crosslinked network.

The cellulosic polymers are chosen more particularly from microcrystalline celluloses such as the products sold under the name "Avicel" by FMC Corporation.

Among the synthetic polymers there may be more particularly mentioned polyethylene, polypropylene, polystyrene, poly(methyl methacrylate) sold under the names "Micropearl M" and "Micropearl M100" by Seppic, crosslinked poly(methyl methacrylate) such as the product sold under the name of "Micropearl M 305" by Seppic. Other polymers are chosen, in particular, from cross-linked poly-β-alanine such as described in French Patent 2,530,250, in which the degree of crosslinking is between 1 and 15% and, preferably, between 1 and 8%.

It is also possible to employ, as polymers, the products known under the name of microsponges, such as crosslinked styrene/divinylbenzene or methyl methacrylate/ethylene glycol dimethacrylate or vinyl stearate/divinylbenzene polymers, such as are described in Patents WO-88/01,164 and U.S. Pat. No. 4,690,825. Such polymers consist essentially of beads of crosslinked polymers comprising an internal pore network capable of retaining the melaninlike pigment.

According to a third embodiment the particulate filler is a filler consisting of organic or inorganic particles with a lamellar structure which are smaller than 50,000 nm in size. The particles of lamellar structure consist of leaflets in the case of which the ratio between the longest dimension and the thickness is particularly between 2 and 100.

Composite melaninlike pigments deposited on a lamellar filler, and their preparation, are described in European Patent Application No. 0,467,767.

The cosmetic composition of the invention may be employed as a composition for protecting the human epidermis, the mucosae or the hair, as a product for making-up the skin or its apparent superficial growths. The tocopherol/melaninlike pigment combination is also useful for protecting cosmetic compositions themselves against free radicals; it is also useful in compositions for oral and dental use, such as toothpastes.

This composition can, in particular, take the form of a lotion, thickened lotion, gel, vesicular dispersion, dispersion of nanoparticles, cream, milk, powder, ointment or solid stick and may optionally be packaged as an aerosol and be in the form of a foam or spray.

The compositions in accordance with the invention may be in the form of a vesicular dispersion of ionic or nonionic amphiphilic lipids. They are prepared especially by swelling lipids in an aqueous solution to form spherules dispersed in the aqueous medium, as described in the paper by Bangham, Standish & Watkins, J. Mol. Biol., 13, 238 (1965) or in the Applicant's patents FR-2,315,991 and 2,416,008.

The various types of processes of preparation are described in "Les liposomes en biologie cellulaire et pharmacologie" ["Liposomes in cell biology and pharmacology"], published by INSERM/John Liberry Eurotext, 1987, pages 6 to 18.

The compositions may be in the form of dispersions of nanoparticles. The term "nanoparticles" covers, on the one hand, nanospheres and, on the other hand, nanocapsules; the term "nanospheres" is used to denote the nanoparticles consisting of a porous polymeric matrix on which the active principle is absorbed and/or adsorbed, and the term "nanocapsules" the nanoparticles consisting of a polymeric membrane which surrounds a core formed by the active principle. Such forms of composition are described, for example, in Patent Applications EP-274,961 and FR-2,659,554.

It may contain cosmetic adjuvants which are usually employed, such as fatty substances, organic solvents, silicones, thickeners, emollients, UV-A, UV-B or broad-band sunscreens, antifoam agents, hydrating agents, perfumes, stabilizers, surfactants, fillers, sequestrants, anionic, cationic, nonionic or amphoteric polymers or mixtures thereof, propellants, alkalifying or acidifying agents, dyes, metal oxide pigments such as iron oxides, or any other ingredient usually employed in cosmetics, as well as self-tanning agents such as dihydroxyacetone.

Among the organic solvents there may be mentioned lower alcohols and polyols such as ethanol, isopropanol, propylene glycol, glycerin and sorbitol. Esters of fatty acids, such as isopropyl myristate, isopropyl adipate, benzoates of $C_{12}$–$C_{15}$ fatty alcohols ("Finsolv TN" from Finetex), myristyl alcohol oxypropylenated with 3 moles of propylene oxide ("Witconol APM" from Witco), and the like, and triglycerides of capric and caprylic acids ("Miglyol 812" from Hüls).

The cosmetic composition according to the invention may therefore contain thickeners which can be chosen from acrylic acid polymers, crosslinked or otherwise, and particularly the polyacrylic acids crosslinked with a polyfunctional agent, such as the products sold under the name "Carbopol" by Goodrich, cellulose derivatives such as methyl cellulose, hydroxyethyl cellulose, hydroxypropyl methyl cellulose, sodium salts of carboxymethyl cellulose, and mixtures of cetyl stearyl alcohol and of cetyl stearyl alcohol oxyethylenated with 33 moles of ethylene oxide.

It is also possible to employ the products resulting from the ionic interaction of a cationic polymer consisting of a copolymer of cellulose and of a cellulose derivative which are grafted with a salt of a water-soluble quaternary ammonium monomer and of a carboxylic anionic polymer, such as are described in French Patent FR-2,598,611. Use is preferably made of the product of ionic interaction of a hydroxyethyl cellulose copolymer grafted by a radical route with diallyldimethylammonium chloride, such as the polymer marketed under the name "Celquat L 200" by National Starch, either with copolymers of ethylene and maleic anhydride such as the products sold under the name "EMA 31" by Monsanto, or with 50/50 copolymers of methacrylic acid and methyl methacrylate.

Another product of this type which can be employed is the product resulting from the ionic interaction of the copolymer of hydroxyethyl cellulose grafted by a radical route with diallyldimethylammonium chloride with a crosslinked carboxylic anionic polymer, such as the crosslinked copolymers of methacrylic acid and ethyl acrylate which are sold under the name "Viscoatex" 538 or 46 by Coatex.

The fatty substances may consist of an oil or a wax or a mixture thereof, fatty acids, fatty alcohols, vaseline, paraffin, lanolin, hydrogenated lanolin, acetylated lanolin, cocoa butter or karité butter.

The oils are chosen from animal, vegetable, mineral or synthetic oils, and especially hydrogenated palm oil, hydrogenated castor oil, vaseline oil, liquid paraffin, purcellin oil, silicone oils and isoparaffins.

The waxes are chosen from animal, fossil, vegetable, mineral or synthetic waxes. Beeswaxes, carnauba and candelilla, sugar cane and Japan waxes, ozokerites, montan wax, microcrystalline waxes, paraffin waxes and silicone waxes and resins may be mentioned in particular.

When the cosmetic composition according to the invention is employed for protecting the human epidermis, it may take the form of suspension or dispersion in solvents or fatty substances, or else the form of emulsion such as a cream or a milk, the form of ointment, gel, solid stick or of aerosol foam.

The emulsions may additionally contain anionic, nonionic, cationic or amphoteric surface-acting agents.

The composition for protecting the human epidermis against free radicals may additionally contain antisolar or self-tanning agents and, in the same forms as above, can be employed as a protective antisolar or self-tanning composition.

When the cosmetic composition according to the invention is employed for the protection of hair, it can take the form of a shampoo, lotion, rinsing gel or composition, to be applied before or after shampooing, before or after dyeing or bleaching, before, during or after permanent waving or straightening, styling or treating lotion or gel, lotion or gel for blow drying or setting, hair lacquer, permanent wave or hair straightening, dyeing or bleaching composition.

When the composition is employed as a make-up product for eyelashes, eyebrows or the skin, such as a cream for treating the epidermis, make-up foundation, lipstick, eye shadow, cheek blush, eyeliner or mascara, it can take an anhydrous or aqueous, solid or pasty form, such as oil-in-water or water-in-oil emulsions or suspensions.

When the composition is employed for the make-up of hair, it can also take anhydrous, or aqueous, solid or pasty form, in the form of oil-in-water or water-in-oil emulsions or else in the form of suspensions or gels, such as styling or make-up gels.

When the composition is employed in an oral-dental care composition, it may include adjuvants and additives which are usual in the case of compositions for oral use and especially surface-active agents, thickening agents, moistening agents and polishing agents such as silica, active agents such as fluorides, and in particular sodium fluoride, and optionally sweetening agents such as sodium saccharinate.

A further subject of the invention is a process for protecting the human epidermis, the mucosae and hair against the detrimental action of free radicals, consisting in applying an effective quantity of the above composition to the latter.

Another subject of the invention is a make-up process consisting in applying the above cosmetic composition to the skin, its apparent superficial growths or the hair.

Another subject of the invention is a process for protecting cosmetic compositions against free radicals, consisting in incorporating therein an effective quantity of the tocopherol/melaninlike pigment combination.

The invention will be illustrated better by the following nonlimiting examples.

EXAMPLE 1

A sun cream of the following composition is prepared:

| | | |
|---|---|---|
| Melanin obtained by oxidation of 5,6-dihydroxyindole | | 0.025 g AS |
| DL-α-Tocopherol (vitamin E) sold by Hoffman La Roche | | 0.5 g |
| 2-Ethylhexyl p-methoxycinnamate sold under the name of "Parsol MCX" by Givaudan | | 5.0 g |
| Mixture (80/20) of cetyl stearyl alcohol and of cetyl stearyl alcohol oxyethylenated with 33 moles of ethylene oxide, sold under the name "Sinnowax AO" by Henkel | | 7.0 g |
| Glycerol mono- and distearate (40/50) sold under the name "Geleol" by Gattefosse | | 2.0 g |
| Cetyl alcohol (90% $C_{16}$) | | 1.5 g |
| Vaseline oil | | 15.0 g |
| Polydimethylsiloxane | | 1.5 g |
| Glycerin | | 3.0 g |
| Stabilizers, perfume | q.s. | |
| Water | q.s. | 100 g |

EXAMPLE 2

A self-tanning cream of the following composition is prepared:

| | | |
|---|---|---|
| Melanin obtained by oxidation of 5,6-dihydroxyindole | | 0.015 g AS |
| DL-α-Tocopherol (vitamin E) sold by Hoffmann La Roche | | 1.0 g |
| Dihydroxyacetone | | 3.0 g |
| Mixture (80/20) of cetyl stearyl alcohol and of cetyl stearyl alcohol oxyethylenated with 33 moles of ethylene oxide, sold under the name "Sinnowax AO" by Henkel | | 7.0 g |
| Glycerol mono- and distearate (40/50) sold under the name "Geleol" by Gattefosse | | 2.0 g |
| Cetyl alcohol (90% $C_{16}$) | | 1.5 g |
| Vaseline oil | | 10.0 g |
| Polydimethylsiloxane | | 1.5 g |
| Glycerin | | 10.0 g |
| Stabilizers, perfume | q.s. | |
| Water | q.s. | 100 g |

EXAMPLE 3

A hair make-up gel of the following composition is prepared:

| | | |
|---|---|---|
| Crosslinked methacrylic acid/ethyl acrylate copolymer in anionic dispersion at a concentration of 38% AS in water, marketed under the name "Viscoatex 538" by Coatex | | 1.6 g AS |
| Hydroxyethyl cellulose/diallyldimethyl-ammonium chloride copolymer marketed under the name "Celquat L200" by National Starch | | 1.6 g |
| Polydimethylsiloxane containing amino-ethylpropylamine groups in cationic emulsion at a concentration of 35% AS in water, marketed under the name "DC 929" by Dow Corning | | 0.3 g AS |
| Ethanol | | 10.0 g |
| DL-α-Tocopherol (vitamin E) sold by Hoffmann La Roche | | 0.1 g |
| Melaninlike pigment obtained by oxidation of 5,6-dihydroxyindole | | 1.0 g |
| Stabilizer, sequestrant | q.s. | |
| Perfume | q.s. | |
| 2-Amino-2-methyl-1-propanol | q.s. | pH 7.5 |
| Demineralized water | q.s. | 100 g |

EXAMPLE 4

A toothpaste which has the following composition is prepared:

| | | |
|---|---|---|
| Silica marketed under the name "Tixosil 73" by Rhône Poulenc | | 12.0 g |
| Silica marketed under the name "Tixosil 333" by Rhône Poulenc | | 8.0 g |
| Sorbitol in solution at a concentration of 70% AS in water | | 14.0 g AS |
| Glycerin | | 5.0 g |
| Carboxymethyl cellulose sold under the name "Blanose 9M 31 F" by Hercules | | 1.4 g |
| Sodium lauryl sulfate at a concentration of 92% of AS in water, sold under the name "Empicol LZV/E" by Marchon | | 1.8 g |
| Sodium fluoride | | 0.22 g |
| Titanium dioxide | | 0.5 g |
| Sodium saccharinate | q.s. | |

-continued

| | | |
|---|---|---|
| Flavoring | q.s. | |
| Vitamin E | | 0.15 g |
| Melaninlike pigment obtained by oxidation of 5,6-dihydroxyindole | | 0.01 g |
| Stabilizer | q.s. | |
| Water | q.s. | 100 g |

EXAMPLE 5

A make-up foundation of the following composition is prepared:

A)

| | |
|---|---|
| Water | 44.80 g |
| Methyl p-hydroxybenzoate | 0.10 g |
| Propylene glycol | 2.00 g |
| Yellow iron oxide | 1.00 g |
| Red iron oxide | 0.40 g |
| Black iron oxide | 0.20 g |
| Titanium oxide | 9.40 g |
| Melanin obtained by oxidation of 5,6-dihydroxy indole | 0.01 g |
| Magnesium silicate and aluminum hydrate | 1.00 g |
| Sodium lauroyl sarcosinate in water at a concentration of 30% sold under the name "Oramix L30" by Seppic | 0.18 g MA |
| Sodium carboxymethyl cellulose | 0.20 g |
| Triethanolamine | 1.00 g |

B)

| | | |
|---|---|---|
| B1 | Stearic acid | 2.20 g |
| | Mixture of glyceryl mono-di-stearate, stearic acid, glycerin (40/50/5/5) sold under the name "Geleol" by Gattefosse | 2.20 g |
| | Triglycerides of caprylic acids sold under the name "Miglyol 812" by Hüls | 15.00 g |
| | Propyl p-hydroxybenzoate | 0.30 g |
| Cyclopenta dimethylsiloxane | | 10.00 g |
| DL-α-tocopherol (vitamin E) sold by Hoffmann La Roche | | 0.09 g |

C)

| | |
|---|---|
| Water | 1.00 g |
| Imidazolidinylurea | 0.30 g |
| Glycerin | 3.00 g |

D)

| | |
|---|---|
| Perfume | 0.20 g |

E)

| | |
|---|---|
| Starch crosslinked with octenylsuccinic anhydride, sold under the name "Dry Flo PC" by National Starch | 5.00 g |

OPERATING METHOD

1) Heating is carried out in a beaker at 95° C. The propylene glycol is introduced and the methyl parahydroxybenzoate is dissolved At 80° C. the pigments are dispersed for 1 hour and then the melanin for 10 minutes. The magnesium silicate and the aluminum hydrate are introduced with stirring. The material is allowed to cool to 70° C. and the Oramix L30 and sodium carboxymethyl cellulose and triethanolamine are added.

2) The ingredients of phase B1 are melted at 80° C. The cyclopentadimethyl siloxane and the vitamin E are added to them. The mixture B is maintained at 65° C.

3) Phase B is poured onto phase A with stirring using the turbine. The mixture is allowed to cool with stirring to 40° C. and phase C, prepared at a temperature of less than 40° C. is added, and then D and E are added with stirring and the temperature is allowed to return to 25° C.

EXAMPLE 6

A mascara of the following composition is prepared:

| | | | |
|---|---|---|---|
| A | Triethanolamine stearate | | 12.0 g |
| | Beeswax | | 4.0 g |
| | Carnauba wax | | 1.5 g |
| | Paraffin wax | | 6.0 g |
| | DL-α-Tocopherol (vitamin E) sold by Hoffmann La Roche | | 0.36 g |
| | Black iron oxide | | 5.0 g |
| | Melanin obtained by oxidation of 5,6-dihydroxyindole | | 0.04 g |
| B | Hydroxyethyl cellulose | | 1.5 g |
| | Gum arabic | | 1.0 g |
| | Polyvinylpyrrolidone | | 1.0 g |
| | Methyl para-hydroxybenzoate | | 0.2 g |
| | Propyl para-hydroxybenzoate | | 0.7 g |
| | Water | q.s. | 100 g |

OPERATING METHOD

The components of phase A are heated to 85° C., the iron oxides and the melanin are added and mixing is then carried out using the turbine.

The water for the preparation is boiled and the stabilizers are dissolved in it and then, at 85° C., the components of phase B are added.

The aqueous phase at 85° C. is added to phase A (80° C.), into which the vitamin E has been introduced while mixing using the turbine. The material is cooled while mixing to 27° C.

EXAMPLE 7

An antisun cream of the following composition is prepared:

| | | |
|---|---|---|
| Melanin obtained by oxidation of 5,6-dihydroxyindole | | 0.08 g |
| Mixture of natural tocopherols in soya oil (50/50) sold under the name "Tocopherol Concentrat Naturel" by Rossow | | 0.04 g |
| 2-Ethylhexyl p-methoxycinnamate sold under the name "Parsol MCX" by Givaudan | | 5.0 g |
| Cetyl alcohol (90% $C_{16}$) | | 15.0 g |
| Polyethylene glycol monostearate containing 50 moles of ethylene oxide, sold under the name "Myrj 53" by ICI | | 3.0 g |
| Glycerol mono- and distearate (40/50) sold under the name "Geleol" by Gattefosse | | 3.0 G [sic] |
| Vaseline oil | | 24.0 g |
| Water | q.s | 100 g |

EXAMPLE 8

A face cream of the following composition is prepared:

| First phase: | |
|---|---|
| Nonionic amphiphilic lipid of general formula: $C_{16}H_{33}\text{---}(O\text{---}CH_2\text{---}CH)_{\overline{3}}\text{---}OH$ with $CH_2OH$ branch | 3.8 g |
| Cholesterol | 3.8 g |
| Dicetyl phosphate | 0.4 g |
| DL-α-Tocopherol (vitamin E) sold by Hoffmann La Roche | 0.05 g |
| Glycerol | 3.0 g |
| Melanin obtained by oxidation of 5,6-dihydroxyindole | 0.01 g |
| Stabilizers q.s. | 0.01 g |
| Water | 52.44 g |
| Second phase: | |
| Macadamia oil | 15.0 g |
| Perfume q.s. | |
| Crosslinked polyacrylic acid sold under the name "Carbopol 940" by Goodrich | 0.4 g |
| Triethanolamine | 0.4 g |
| Water | 20.0 g |

The first phase is prepared as follows: the lipids are mixed at 95° C. in the molten state. Vitamin E is added to them. The aqueous phase (glycerol+water) is heated to 80° C. Part of the aqueous phase is mixed into the lipid phase with gentle stirring to form a lamellar phase. The remainder of the aqueous phase is added to form the dispersion phase. The melanin and the stabilizers are added. Stirring is continued until a concentrated vesicular suspension is obtained. This is homogenized in order to reduce the size of the vesicles (mean diameter around 200 nm).

The second phase is then added, the macadamia oil being first dispersed by mechanical stirring at 40° C., then the perfume, the "Carbopol 940", the triethanolamine and the water being incorporated.

EXAMPLE 9

A body cream of the following composition is prepared:
1) Preparation of a dispersion of nanoparticles 250 mg of a condensate of ethylene oxide and propylene oxide (20/80%), with a mean molecular weight of 1750 and 8350 respectively, sold under the trade name of "Pluronic F68" by BASF, are dissolved in 50 ml of demineralized water in a 100-ml beaker, with stirring provided by a magnetic bar rotating at 400 rev/min. Into this aqueous phase, thermostatted at a temperature of 40° C., are slowly poured 25 ml of acetone, in which 250 mg of soya lecithin, sold under the trade name "Epikuron 170" by Lucas Meyer have been previously dissolved at a temperature of 55° C. and then, after returning to a temperature of 40° C., the following are dissolved:

500 mg of a tocopherol mixture in soya oil (50/50) sold under the name "Tocopherol Concentrat Naturel" by Rossow.

125 mg of polycaprolactone marketed by Aldrich.

Stirring is maintained for 2 hours at a temperature of 40° C., followed by a return to room temperature. The nanoparticle dispersion obtained is then transferred into a 250-ml round bottom flask which is placed on a rotary evaporator and the acetone is evaporated off. A fluid, colloidal dispersion of nanoparticles whose mean diameter is 195 nm is thus obtained.

On examination with a microscope, in white light, a dense population of nanoparticles which are uniform in size is observed.

2) Preparation of a dispersion of vesicles 0.05 g of dimyristyl phosphate and 0.95 g of nonionic surfactant of formula (I) are weighed into a 100-ml glass beaker: —Nonionic lipid of formula:

$$C_{12}H_{25}\text{---}(OC_2H_3(R))\text{---}O\text{---}(C_3H_5\text{---}OH)\text{---}O\text{---}_{\overline{n}}H$$

in which formula:

* $-C_3H_5(OH)O-$ consists of a mixture of radicals:

$$-CH_2-CHO- \quad \text{and} \quad -CH-CH_2O-$$
$$\quad\quad\quad |\quad\quad\quad\quad\quad\quad\quad\quad |$$
$$\quad\quad CH_2OH \quad\quad\quad\quad\quad CH_2OH$$

* $-O-C_2H_3(R)-$ consists of a mixture of radicals $$-O-CH-CH_2- \quad \text{and} \quad -O-CH_2-CH-$$
$$\quad\quad |\quad\quad\quad\quad\quad\quad\quad\quad\quad\quad\quad |$$
$$\quad\quad R\quad\quad\quad\quad\quad\quad\quad\quad\quad\quad\quad R$$

* $\overline{n}$ is a mean statistical value equal to 2.7, determined by $^1$HNMR at 500 MHz,

* R is a mixture of radicals $C_{14}H_{29}$ and $C_{16}H_{33}$

These two lipids are homogenized by heating on a hotplate at a temperature of 100° C. and the mixture is then cooled to 40° C. 27.575 g of water in which 3 g of glycerin and 0.02 g of citric acid have previously been dissolved are then added. The whole is homogenized by the action of an ultradisperser of "Virtis" type for 2 minutes at a speed of 40,000 rev/min, at a temperature of 40° C. 3 g of water are then added, in which 0.1 g of stabilizer sold under the trade name "Kathon CG" by Rhom [sic]& Haas and 0.2 g of stabilizer sold under the trade name "Germal 115" by Rhom [sic]& Haas and 0.025 g of melanin obtained by oxidation of 5,6-dihydroxyindole have previously been dissolved.

The fatty phase made up of a mixture of the following products is then added:

| Macadamia oil | 9.0 g |
|---|---|
| Poultry [sic] silicone oil | 7.0 g |
| Ethylhexyl para-methoxycinnamate sold under the trade name "Parsol MCX" by Givaudan | 0.5 g |
| 2-Hydroxy-4-methoxybenzophenone sold under the trade name "Uvinul M 40" by BASF | 0.5 g |
| Propyl para-hydroxybenzoate | 0.05 g |

The whole is subjected to the action of the "Virtis" ultradisperser for 5 minutes at room temperature.
3) Mixture of the vesicle and nanoparticle dispersions 20 g of the aqueous dispersion of nanoparticles, prepared previously, are added to the dispersion of vesicles. 35 g of water are then added, in which 0.65 g of carboxyvinylic acid sold under the trade name "Carbopol 940" by Goodrich have been swollen. After homogenization, 0.65 g of triethanolamine diluted with 1.73 g of water are finally added. A thick, white cream of glossy appearance, intended for body care, is thus obtained. After an application of this cream, once daily for a fortnight, an improvement in the surface quality of the treated skin is observed.

We claim:

1. A cosmetic composition protecting the human epidermis, the mucosae and the hair against free radicals comprising the combination in a cosmetically acceptable carrier of at least one tocopherol selected from the group consisting of α-tocopherol, β-tocopherol, γ-tocopherol, and δ-tocopherol in a concentration of between 0.02 and 10% by weight relative to the total weight of the composition, and at least one natural or synthetic melanin pigment in a concentration of between 0.001 and 2% by weight relative to the total weight of the composition, the weight ratio of tocopherol to melanin pigment being between 0.1 and 100.

2. Cosmetic composition according to claim 1, wherein the tocopherol is vitamin E.

3. Cosmetic composition according to claim 1, wherein the melanin pigment is obtained by oxidation of at least one indole derivative of the formula:

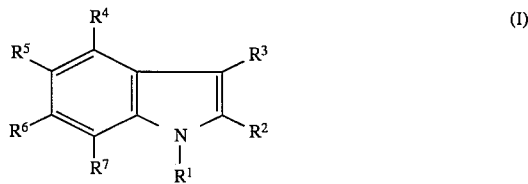

in which:

$R^1$ and $R^3$ denote, independently of one another, a hydrogen atom or a $C_1$–$C_4$ alkyl group, $R^2$ denotes a hydrogen atom, a $C_1$–$C_4$ alkyl group, a carboxyl group or a $C_1$–$C_4$-alkoxycarbonyl group; $R^4$ and $R^7$ denote, independently of one another, a hydrogen atom, a hydroxyl group, a $C_1$–$C_4$ alkyl group, an amino group, a $C_1$–$C_4$ alkoxy group, a $C_2$–$C_4$ acyloxy group or a $C_2$–$C_4$ acylamino group; $R^5$ denotes a hydrogen atom, a hydroxyl group, a $C_1$–$C_4$ alkoxy group, a $C_1$–$C_4$ alkyl group, a halogen atom, an amino group, a $C_2$–$C_{14}$ acyloxy group, a $C_2$–$C_4$ acylamino group or a trimethylsilyloxy group; $R^6$ denotes a hydrogen atom, a hydroxyl group, a $C_1$–$C_4$ alkoxy group, an amino group, a $C_2$–$C_4$ acyloxy group, a $C_2$–$C_4$ acylamino group, a trimethylsilyloxy group or a $C_2$–$C_4$ hydroxyalkylamino group; it being also possible for $R^5$ and $R^6$ to form, together with the carbon atoms to which they are attached, a methylenedioxy ring unsubstituted or substituted by a $C_1$–$C_4$ alkyl or $C_1$–$C_4$ alkoxy group, or a carbonyldioxy ring; at least one of the radicals $R^4$ to $R^7$ denotes a group OZ or $NHR^0$ not more than one of the radicals $R^4$ to $R^7$ denoting $NHR^0$ and not more than two of the radicals $R^4$ to $R^7$ denoting OZ and, in the case where Z denotes a hydrogen atom, the two OH groups are in positions 5 and 6; and at least one of the radicals $R^4$ to $R^7$ denotes a hydrogen atom, and in the case where only one of these radicals denotes hydrogen atom, only one radical among the radicals $R^4$ to $R^7$ then denotes $NHR^0$ or OZ, the other radicals denoting a $C_1$–$C_4$ alkyl group; the radical $R^0$ of the group $NHR^0$ denoting a hydrogen atom, a $C_2$–$C_4$ acyl or $C_2$–$C_4$ hydroxyalkyl group, and the radical Z of the group OZ denoting a hydrogen atom, a $C_2$–$C_{14}$ acyl group, a $C_1$–$C_4$ alkyl group or a trimethylsilyl group; and the alkali metal, alkaline-earth metal, ammonium or amine salts of this indole derivative.

4. Cosmetic composition according to claim 3, wherein the indole derivative is selected from the group consisting of 4-hydroxyindole, 5-hydroxyinodole, 6hydroxyindole, 7-hydroxyindole, 4-hydroxy-5-methoxyindole, 4-hydroxy-5ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole 5-hydroxy-2-ethoxycarbonylindole, 6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-dimethoxyindole, 5,6-methylenedioxyindole, 5,6-trimethylsilyloxyindole, the phosphoric ester of 5,6-dihydroxyindole, 5,6-dibenzyloxyindole, and the addition salts of these compounds.

5. Cosmetic composition according to claim 3, wherein the indolelike derivative is 5,6-dihydroxyindole.

6. Cosmetic composition according to claim 1, wherein the composition is in the form of a lotion, thickened lotion, gel, vesicular dispersion, dispersion of nanoparticles, cream, milk, powder, ointment, solid stick, foam or spray.

7. Cosmetic composition according to claim 6, wherein the composition additionally contains cosmetic adjuvants selected from the group consisting of lower alcohols, polyols, esters of, fatty acids, oils, and waxes, solvents, silicones, thickeners, emollients, UV-A, UV-B and broad band sunscreens, antifoam agents, hydrating agents, perfumes, stabilizers, surfactants, fillers, sequestrants, anionic, cationic, nonionic and amphoteric polymers and mixtures thereof, propellants, alkalifying and acidifying agents, dyes and metal oxide pigments.

8. Cosmetic composition according to claim 1, comprising a composition protecting the human epidermis against free radicals wherein the composition is in a form selected from the group consisting of a suspension, dispersion in solvents, dispersion in fatty substances, an emulsion, a cream, a milk, an ointment, a gel, a solid stick and an aerosol foam.

9. Cosmetic composition according to claim 1, wherein the melanin pigment is present in the composition in a concentration of between 0.005 and 0.5% by weight relative to the total weight of the composition.

10. Cosmetic composition according to claim 1, wherein the tocopherol is present in the composition in a concentration of between 0.02 and 6% by weight relative to the total weight of the composition.

11. A cosmetic composition protecting the human epidermis, the mucosae and the hair against free radicals comprising the combination in a cosmetically acceptable carrier of at least one tocopherol selected from the group consisting of α-tocopherol, β-tocopherol, γ-tocopherol, and δ-tocopherol in a concentration of between 0.02 and 6% by weight relative to the total weight of the composition, and at least one natural or synthetic melanin pigment in a concentration of between 0.005 and 0.5% by weight relative to the total weight of the composition, the weight ratio of tocopherol to melanin pigment being between 0.5 and 50.

12. Cosmetic composition according to claim 11, wherein the tocopherol is vitamin E.

13. Cosmetic composition according to claim 11, wherein the tocopherol is DL-$\alpha$-tocopherol.

14. Cosmetic composition according to claim 11, wherein the tocopherol is a mixture of $\alpha$-tocopherol, $\beta$-tocopherol, $\gamma$-tocopherol and $\delta$-tocopherol.

15. Cosmetic composition according to claim 11, wherein the melanin pigment is obtained by oxidation of 5,6-dihydroxyindole.

16. Cosmetic composition according to claim 11, wherein the composition is in the form of a cream.

* * * * *